United States Patent [19]

Gauri et al.

[11] 4,322,404

[45] Mar. 30, 1982

[54] PROCESS FOR THE PRODUCTION OF NEW MUTANTS OF HERPES SIMPLEX VIRUS TYPE 1 AND TYPE 2

[76] Inventors: Kailash K. Gauri, Zur Waldburg 13, 2359 Lentfohrden; Klaus Pressler, Mikrobiologe, Forellenweg 23, 4800 Bielefeld 1; Klaus-Dirk Schenk, Mikrobiologe, Heinestrasse 6, 4803 Steinhagen, all of Fed. Rep. of Germany

[21] Appl. No.: 271,106

[22] Filed: Jun. 8, 1981

[30] Foreign Application Priority Data

Jun. 12, 1980 [GB] United Kingdom ............... 19308/80

[51] Int. Cl.³ ..................... A61K 39/12; C12N 7/06
[52] U.S. Cl. ..................................... 424/89; 435/237; 435/238
[58] Field of Search ........................... 435/238; 424/89

[56] References Cited

U.S. PATENT DOCUMENTS 4,191,745  4/1980  Mayr et al. ........................... 424/89

OTHER PUBLICATIONS

Helgstrand et al.–Chem. Abst. vol. 92 (1980), p. 42112 t.
Schwoebel et al.–Chem. Abst. vol. 91 (1979), pp. 186, 482 r.
DeClercq et al.–Chem. Abst. vol. 89 (1978), p. 99707 h.
Eriksson, Antimicrobial Agents and Chematherapy, Jun. 1979, pp. 758-762.
Mayer et al., Virologische Arbeitsmelthoden, vol. 1, (1974), pp. 25-33 and 43-93.
Mauersberger Aktuelle Probleme der Zellzuchtung, 1971, pp. 17-60.

*Primary Examiner*—Sam Rosen
*Attorney, Agent, or Firm*—Cushman, Darby & Cushman

[57] ABSTRACT

Herpes virus was doubly mutated in two steps by treatment with phosphono formic acid and 5-ethyl-2'-desoxyuredine. In this way the pathogenicity of the herpes virus was so weakened that they are usable as vaccines.

14 Claims, No Drawings

PROCESS FOR THE PRODUCTION OF NEW MUTANTS OF HERPES SIMPLEX VIRUS TYPE 1 AND TYPE 2

BACKGROUND OF THE INVENTION

The therapy of herpes infection for several reasons presents an important problem. Relapsing infections not only are irksome but can lead with manifestations in certain areas to serious neoplastic changes, for example abdominal cancer in women. For treatment of herpes infections there are used chemotherapeutics as well as herpes vaccines of inactivated, i.e. killed herpes simplex viruses of Type 1 or Type 2. However, the effectiveness of this agent in many cases is not satisfactory.

SUMMARY OF THE INVENTION

The invention consists of subjecting herpes simplex virus of Type 1 and Type 2 to a double mutation by treating in two mutation steps with phosphono formic acid and 5-ethyl-2'-desoxyuredine as a result of which the pathogenicity is lost but the antigen properties are maintained.

In contrast to the vaccines used to the present time for the treatment of herpes the herpes virus mutants thus obtained are living and therefore effect a better immunization.

It is indeed known that the treatment of the Aujeszky virus belonging to the group of herpes virus can lead to a weakening of the pathogenicity of the virus (Zentralblatt fur Veterinarmedizin, B, 15, 847-553, 1968); but the thus obtained virus is still much too virulent to be employed as a vaccine.

The process of the invention consists of treating normal herpes virus of Type 1 (Strain C 42) and Type 2 (Strain CAM 13) which can be obtained from human or animal organism and can contain varying contents of different mutants in two mutation steps, first with phosphono formic acid for example and subsequently with 5-ethyl-2'-desoxyuredine or reversely.

The normal herpes virus used as starting materials are known and can be isolated in known manner from humans or animals either "in vitro" or cultivated or enriched under "in vivo" conditions.

For example the production of such herpes virus usable as starting materials is described in the following literature:

A. Mayr, P. Bachmann, B. A. Bibreck, G. Wittmann: Virolagische Arbeitsmethoden, Vol. 1, pages 25 et seq. 1974, G. Fischer Verlag, Stuttgart. The entire disclosure of this literature is hereby incorporated by reference and relied upon.

The carrying out of the process of the invention takes place by culturing the herpes simplex virus of Type 1 or Type 2 in vivo or in vitro, preferably in vitro (in tissue culture) in two steps, for example first in the presence of phosphono formic acid and subsequently in the presence of 5-ethyl-2'-desoxyuredine or reversely and several passages are carried out in their presence. The treatment with phosphono formic acid generally takes place via 3 to 6 passages, the treatment with 5-ethyl-2'-desoxyuredine generally via 3 to 10 passages.

As tissue cultures for the culturing there can be used the cultures usually suited for the propagation of viruses, especially the propagation of herpes virus. These types of cultures are described for example in A. Mayr et al, Virologische Arbeitsmethoden, Vol. 1 pages 43 et seq., B. Mauersberger, Aktuelle Probleine der Zellzuchtung, 1971, G. Fischer Verlag, Stuttgart. The entire disclosure of Mayr et al and Mauersberger are hereby incorporated by reference and relied upon.

For example there can be employed as cultures for the propagation and cultivation: chicken embryo fibroblast cultures, VERO cell cultures (African Green Monkey kidney cell cultures); rabbit renal cell cultures; BHK-21-cultures (Syrian Baby Hamster Kidney).

The phosphono formic acid is used for example in a concentration of 20 to 50 $\mu$g/ml, the 5-ethyl-2'-desoxyuredine for example in a concentration of 5 to 20 $\mu$g/ml.

The concentration of the herpes virus employed should be sufficiently strong that it infects an adequate cell population and permits as many virus propagation cycles as possible; however, it must not be so high that the entire cell population perishes after a few virus propagation cycles and consequently limits the duration of activity of the mutation producing materials. Preferably the concentration of the herpes virus employed is between 1 $ID_{50}$ and 1000 $ID_{50}$.

The treatment with phosphono formic acid and 5-ethyl-2'-desoxyuridine is at a temperature between 20° and 40° C., preferably from 25° to 37° C., especially 30° to 37° C.

As starting virus for the process of the invention there can be employed herpes simplex viruses of Type 1 and Type 2 from natural human or animal isolation without eliminating the naturally occurring mutants contained therein.

The following table shows the immunization of mice with a herpes simplex vaccine which was obtained according to Example 1. For the production of the vaccine there was employed herpes simplex virus Type 1, Strain C 42. The immunization was carried out by intramuscular injection. The evaluation of the immunoprotection was carried out at different virus titers 30 days after the inoculation by intracerebral infection with herpes simplex virus Type 1 Starting Strain C 42. With the non-immunized animals there arose an encephalitis because of the infection with the starting strain. The treatment with phosphono formic acid and 5-ethyl-2'-desoxyuridine can be in any order.

The results are set forth in the following table.

| Titer of the Herpes simplex-Virus Strain C 42 With Reinfection 30 Days After the Immunization | Ratio of The Number of Dead Mice To The Total Number of Mice | |
|---|---|---|
| | Non-immunized Controls | Immunized With Vaccine According Example 1 |
| $10^{-0}$ | 3/3 | 0/3 |
| $10^{-1}$ | 3/3 | 0/3 |
| $10^{-2}$ | 1/2 | 0/2 |
| $10^{-3}$ | 1/2 | 0/3 |
| $10^{-4}$ | 3/3 | 0/3 |

As the results of the table show all of the animals which were immunized with the weakend virus mutants survived. With renewed infection with the starting virus strain thus these animals are completely immune.

The vaccines of the present invention can be used to immunize all animals subject to infection by herpes simplex virus, e.g. mammals such as mice, monkeys, humans, rabbits, hamsters, etc.

The use of the mutants obtained according to the invention for fighting herpes illnesses takes place in the usual manner for vaccines, for example by injection, through inoculation by swallowing, in the form of sprays as well as in the form of drops, eye drops, nose drops. The herpes mutant produced according to the invention especially causes an immunization against the virus used in each case as the starting virus.

The mutated viruses obtained according to the invention are purified by the usual processes for the production of vaccines (filtration, especially molecular filtration and gel filtration, separation, gradient-centrifugation, adsorption and subsequent elution etc.), in a given case concentrated (zone centrifugation, molecular filtration, adsorption and subsequent elution), stabilized by the addition of stabilizers and made stable with suitable preservatives (e.g. benzyl alcohol, chlorobutanol, Thiomerosal, phenol, cresol).

Furthermore the antigenicity of the vaccine can be reinforced by the addition of adjuvants or be produced by a depot effect.

For this purpose there can be used for example Freund's adjuvant, oily and other organic adjuvants, however, especially aluminum compounds such as aluminum oxide, aluminum hydroxide and aluminum phosphate.

The herpes virus mutants likewise can be used as components of combination vaccines.

The compositions can comprise, consist essentially of or consist of the stated materials and the process can comprise, consist essentially of or consist of the steps set forth with such materials.

DETAILED DESCRIPTION

EXAMPLE 1

The herpes simplex virus Type 1, Strain C 42 employed as starting virus was isolated from a keratitis and passed eight times in baby hamster kidney cells (BHK) using Eagles medium having 7% foetal calves serum (Flow). The herpes virus titer was determined with the help of the plaque test or through titration of the zytopathic effect in primary chicken embryo fibroblasts (see also B. Eriksson and B. Oberg, Antimikrobial Agents and Chemotherapy 1979, pages 758 et seq., the entire disclosure of which is hereby incorporated by reference and relied upon).

The thus obtained virus strain was then inoculated with a multiplicity of a plaque forming units per cell on chicken embryo fibroblasts-monolayer in tissue culture until the dosage of 100 $ID_{50}$ (infectious dosage 50; the dosage at which 50% of the animals are infected) is reached. Then there is added phosphono formic acid dissolved in Eagle's Basal Medium having a content of 2% of foetal calves serum in a concentration of 5 to 50 grams, preferably 20 to 50 grams per ml. As soon as the cells showed a zytopathic effect, the cultures were frozen and thawed and 2 ml were used to infect new chicken embryo fibroblast-monolayers. This was repeated five times so that in all there occurred six passages.

The concentration of the phosphono formic acid in the individual passages were:

| | |
|---|---|
| In the first passage | 20 to 50 μg/ml |
| In the second passage | 20 to 55 μg/ml |
| In the third passage | 20 to 50 μg/ml |
| In the fourth passage | 20 μg/ml |
| In the fifth passage | 20 μg/ml |
| In the sixth passage | 10 μg/ml. |

Then there took place the passage in the presence of α or β-5-ethyl-2'-desoxyuredine (EdU) in concentrations of 5 to 20 g/ml over 3 to 5 passages with the mutants from the sixth passage. The concentrations of the 5-ethyl-2'-desoxyuredine were:

| | |
|---|---|
| In the first passage | 20 μg/ml |
| In the second passage | 20 μg/ml |
| In the third passage | 5 μg/ml |

All the passages mentioned in this example were carried out at 37° C.

The resulting live virus was characterized as antigen for the immunization against herpes illnesses. For example with mice this antigen produced no pathogenic condition but instead leads to the development of an immunity, so that the animals are protected against intrcerebral infection with normal herpes simplex virus of Type 1.

If in place of the herpes simplex virus Type 1 Strain C 42 there is employed as starting material herpes simplex virus Type 2 Strain CAM 13, otherwise the same treatment conditions being carried out as previously given in Example 1 then there are likewise obtained mutated viruses which are usable for the immunization against herpes infections.

What is claimed is:

1. A process for the production of mutated herpes virus comprising treating herpes simplex virus Type 1 or herpes simplex virus Type 2 in two steps with phosphono formic acid and with 5-ethyl-2'-desoxyuredine.

2. Mutated herpes virus produced according to claim 1.

3. A vaccine for fighting herpes infections containing the mutants of herpes virus obtained according to claim 1.

4. A process of immunizing an animal subject to herpes simplex virus infection comprising giving the animal a dosage of a vaccine of claim 3 in an amount effective to immunize against herpes simplex virus.

5. A process according to claim 1 wherein the treatment includes a series of at least 3 successive cell passages wherein each cell passage is treated with phosphono formic acid and the series of passages treated with phosphono formic acid is followed up by a series of at least 3 successive cell passages wherein each cell passage is treated with 5-ethyl-2'-desoxyuredine.

6. A process according to claim 5 wherein there are 3 to 6 passages through cells treated with phosphono formic acid and 3 to 10 passages through passages treated with 5-ethyl-2'-desoxyuredine.

7. A process according to claim 6 wherein there are employed passages through tissue culture.

8. A process according to claim 7 wherein as the tissue culture there is employed chicken embryo fibroblasts.

9. A process according to claim 1 wherein the phosphono formic acid is employed in a medium at a concentration of 5 to 50 μg/ml and the 5-ethyl-2'-desoxyuredine is employed in a medium at a concentration of 5 to 20 μg/ml.

10. A process according to claim 9 wherein the concentration of phosphono formic acid is 20 to 50 μg/ml.

11. A process according to claim 10 wherein the concentration of the herpes virus employed is between 1 $ID_{50}$ and 1000 $ID_{50}$.

12. A process according to claim 9 wherein the concentration of the herpes virus employed is between 1 $ID_{50}$ and 1000 $ID_{50}$.

13. A process according to claim 5 wherein the concentration of the herpes virus employed is between 1 $ID_{50}$ and 1000 $ID_{50}$.

14. A process according to claim 1 wherein the concentration of the herpes virus employed is between 1 $ID_{50}$ and 1000 $ID_{50}$.

* * * * *